(12) United States Patent
Fisher et al.

(10) Patent No.: US 8,715,708 B2
(45) Date of Patent: May 6, 2014

(54) CYCLIC ACETAL BIOMATERIALS

(75) Inventors: John Patrick Fisher, Washington, DC (US); Sachiko Kaihara, Saitama (JP); Jennifer Lynn Moreau, Curtis Bay, MD (US); Parth Modi, Cherry Hill, NJ (US)

(73) Assignee: University of Maryland, College Park, MD (US)

( * ) Notice: Subject to any disclaimer, the term of this patent is extended or adjusted under 35 U.S.C. 154(b) by 1271 days.

(21) Appl. No.: 11/513,401

(22) Filed: Aug. 31, 2006

(65) Prior Publication Data

US 2007/0059337 A1 Mar. 15, 2007

Related U.S. Application Data

(60) Provisional application No. 60/712,980, filed on Aug. 31, 2005.

(51) Int. Cl.
*A61F 2/00* (2006.01)
*A61K 31/00* (2006.01)
*A61K 31/74* (2006.01)
*A61K 47/48* (2006.01)

(52) U.S. Cl.
USPC ............. 424/426; 424/78.17; 424/78.18; 424/78.19; 424/78.3; 424/78.31; 424/78.32

(58) Field of Classification Search
None
See application file for complete search history.

(56) References Cited

U.S. PATENT DOCUMENTS

| 3,993,675 A * | 11/1976 | Uskokovic et al. ........... 540/114 |
| 4,443,619 A * | 4/1984 | Guthrie et al. ............... 549/518 |
| 4,668,779 A * | 5/1987 | Brochon et al. .............. 536/121 |
| 5,443,950 A | 8/1995 | Naughton et al. |
| 6,514,972 B2 * | 2/2003 | Zhang et al. .................. 514/243 |
| 6,652,883 B2 * | 11/2003 | Goupil et al. ................. 424/489 |
| 7,329,414 B2 * | 2/2008 | Fisher et al. .................. 424/426 |
| 2004/0028804 A1 * | 2/2004 | Anderson et al. ........... 427/2.11 |
| 2005/0038109 A1 * | 2/2005 | Stewart et al. ............... 514/492 |
| 2007/0269482 A1 * | 11/2007 | Sebree et al. ................. 424/423 |
| 2008/0035337 A1 * | 2/2008 | Reddy et al. .................. 166/276 |

OTHER PUBLICATIONS

"Biomaterial." Meriam Webster's Online Dictionary. Retrieved from (www.merriam-websters.com) on Nov. 27, 2009, p. 1.*
Anderson, David G.; Lynn, David M.; Langer, Robert; Semi-Automated Synthesis and Screening of a Large Library of Degradable Cationic Polymers for Gene Delivery; 2003; Wiley-WCH GmbG & Co.; Angew. Chem. Int. Ed., 2003, vol. 42, pp. 3153-3158.*
Falco et al.; "Recent Developments in Cyclic Acetal Biomaterials for Tissue Engineering Applications", 2008, Springer; Pharmaceutical Research, vol. 25, No. 10, pp. 2348-2356.*

(Continued)

*Primary Examiner* — Suzanne Ziska
*Assistant Examiner* — Ivan Greene
(74) *Attorney, Agent, or Firm* — Leydig, Voit & Mayer, Ltd.

(57) ABSTRACT

A novel class of Cylic Acetal biomaterials (CABs) based on a cyclic acetal unit is disclosed and claimed by Applicants. Two novel biomaterials suitable for use in a variety of biological applications including in the orthopedic field for joint and cartilage replacement and/or repair, and bone cement. The biomaterials are comprised of either a network of monomers of 5-ethyl-5-(hydroxymethyl)-β,β-dimethyl-1,3-dioxane-2-ethanol diacrylate (EHD) and a hydrogel comprised of EHD and poly(ethylene glycol) diacrylate (PEG-EHD).

7 Claims, 13 Drawing Sheets

(56) References Cited

OTHER PUBLICATIONS

Kaihara et al.; "Synthesis and characterization of cyclic acetyl based", 2007, Elsevier; European Journal of Pharmaceutics and Biopharmaceutics, vol. 68, Issue 1, pp. 67-73.*

Moreau et al.; "Synthesis and properties of cyclic acetal biomaterials", 2006; Wiley-InterScience; Journal of Biomedical Materials Research, vol. 81A, Issue 3, pp. 594-602.*

Sigma Aldrich product information for poly(ethylene glycol) and poly(ethylene glycol) diacrylate retrieved from <www.sigmaaldrich.com> on May 10, 2013, pp. 1-2, as provided.*

* cited by examiner

CYCLIC ACETAL BIOMATERIALS

CROSS-REFERENCE TO RELATED APPLICATIONS

This patent application claims priority to U.S. provisional patent application Ser. No. 60/712,980 filed Aug. 31, 2005, and is incorporated by reference herein as if set forth in its entirety.

BACKGROUND OF THE INVENTION

1. Field of Invention

This invention relates to the field of tissue engineering. More specifically, it relates to novel 3-dimensional hydrogel scaffolds which support the growth and maintenance of cells in culture, for use in simulated organ and tissue function, the study of cell-cell and cell-matrix interactions, development and testing of biological, pharmaceutical and biochemical compounds, as well as components of medical devices and apparatus.

2. Description of Prior Art

Tissue engineering seeks to repair, replace or restore tissue and/or organ function, typically by combining biomaterials and living cells.

There are many materials that are currently being used in tissue engineering applications. Natural polymers that have been used in this field include agarose, chitosan, hyaluronic acid, collagen, gelatin, and silk. Synthetic polymers have also been used for tissue engineering applications, including poly (L-lactic acid), poly(glycolic acid), poly(D,L-lactic acid-co-glycolic acid) and poly(caprolactone), poly(propylene fumarate), poly(orthoester), poly(anhydride), poly(ethylene glycol), poly(ethylene oxide), poly(methyl methacrylate) and poly(urethane).

These natural and synthetic polymers when used in tissue related applications, are often referred to as biomaterials. Biomaterials are used in a variety of related applications, such as in the orthopedic field for joint and cartilage replacement and repair. Biomaterials can be used in applications such as bone cement, artificial ligaments and tendons, vascular grafts, heart valves, stents, and blood substitutes. Further uses for biomaterials can be artificial lenses, degradable sutures, dental implants, burn dressings, artificial skin, and as a drug or biologic delivery device.

The inherent properties of the biomaterial used in a tissue engineered construct emerge from the local response of the cells to their 3-dimensional microenvironment. It is therefore of great importance to re-create biochemical and structural components of the in vivo cellular microenvironments when designing implantable tissue constructs. This microenvironment can be simulated by patterning of the matrix in which the cells are grown in or on, or by patterning the cells within the matrix. For example, scaffold texture can alter cell migration, ingrowth, vascularization, and host integration. Microscale scaffold architecture can also modify the cellular responses such as growth and differentiation as has been shown on three-dimensional polymer meshes (e.g. U.S. Pat. No. 5,443,950).

Methods to prepare scaffolds with microscale structure that are more amenable to use with biodegradable polymers such as poly-DL-lactide-co-glycolide (PLGA) have also been developed. Material microstructure was first controlled by process parameters such as the choice of solvent in phase separation, doping with particulate leachants, gas foaming, woven fibers, and controlled ice crystal formation and subsequent freeze-drying to create pores; however, these scaffolds lack a well-defined organization that is found in most tissues in vivo (i.e. pores are randomly distributed rather than oriented and organized in functional units). Similarly, microtubular scaffolds, 3-dimensional micropatterned scaffolds using UV polymerization, can also produce scaffolds with arbitrary architectures.

Hydrogels are becoming an increasingly popular material for tissue engineering because their high water content and mechanical properties resemble those of tissues of the body. In addition, many hydrogels can be formed in the presence of cells by photopolymerization, which allows homogeneous suspensions of cells throughout the gel. Poly (ethylene glycol) (PEG)-based hydrogels are of particular interest because of their biocompatibility, hydrophilicity and the ability to be customized by changing the chain length or chemically adding biological molecules. PEG based hydrogels have been used to homogeneously immobilize various cell types including chondrocytes, vascular smooth muscle cells, and fibroblasts that can attach, grow and produce matrix.

Generally, it is understood in the art that the synthetic biomaterial should provide a matrix for the biological tissue to fill and then slowly degrade and be absorbed by the tissue. Few synthetic degradable biopolymers have been studied for use in tissue engineering applications. Generally, the degradable synthetic polymers developed were intended for use in plastics that are biodegradable in the environment. Most of the chemistry of degradable biopolymers is based on an ester polymer backbone. Such materials include poly(L-lactic acid) (PLLA), poly(glycolic acid) (PGA), poly(D,L-lactic acid-glycolic acid)(PLGA), poly(propylene glycol-co-fumaric acid) (PPF) and poly(caprolactone) (PCL). Polymer materials like these degrade when in the presence of water, as a result of the water molecule reacting with the ester linkage of the polymer backbone.

PLLA is attractive as a biomaterial because there exists outstanding possibilities for the modification of its properties via copolymerization and stereocopolymerization and compounding. PLLA has a hydrophobic nature, and as such allows for protein absorption and cell adhesion, making it a suitable biomaterial for tissue engineering purposes. PGA has been shown to exhibit increased cell attachment properties when compared to PLLA. PLGA, the copolymer of PLLA and PGA, has mechanical properties and a degradation rate that can be controlled by adjusting the ratio of PLLA: PGA. PLLA, PGA, and PLGA are Food and Drug Administration-approved and are currently being used as biomaterials for tissue engineering applications, as resorbable sutures, as bone plates and screws, and in drug delivery devices. PPF is covalently crosslinked by means of its double bond, leading to increased mechanical properties. Additionally, PPF is attractive because its crosslinking is photoinitiated and can therefore be cured in situ. PCL is favorable as a biomaterial because its properties can be tailored by copolymerization with collagen, PGA, and poly(ethylene oxide). It is important, however, that all of the chains of a synthesized polymer be identical because chain length is a determining factor of the degradation properties of a biomaterial.

Another property of synthetic polymers is that their mechanical properties can be compromised as they degrade. Aside from mechanical degradation, the major disadvantage to the use of the prior art biomaterials in biological tissue applications is that their degradation products are acidic. As the scaffold degrades, the local pH of the tissue becomes quite acidic. The acidity initiates an immune response from the recipient that leads to increased inflammation at the site. The corresponding inflammation results in further premature degradation of the biopolymer scaffold.

There have been reports of concern raised about the biocompatibility of these materials have been raised when PLA and PGA produced toxic solutions as a result of acidic degradation in situ.

As such, there exists in the art a need for development of a biocompatible, water-soluble biomaterial, which does not produce acidic or toxic byproducts as a result of biodegradation or absorption in the host tissues.

SUMMARY OF THE INVENTION

In accordance with the present invention, it has been discovered by Applicants, that novel cyclic acetyl biomaterials (CABs) can be made which are both derived from a network of monomers of compounds having hydrolytically degradable cyclic acetal units. FIG. 1 shows the CAB monomer subunit of the biomaterials of the present invention.

In FIG. 1, $R_1$, is independently selected from hydrogen or from straight chain or branched, saturated or unsaturated $C_{1-8}$, hydrocarbon optionally substituted by one or more hydroxy, halo, aryl, cyclo $C_{1-8}$ alkyl, and $R_2$ and $R_3$ both have terminal acrylate groups designated as $R_4$—OOCHC=$CH_2$, wherein $R_4$ is independently selected from hydrogen or halo; or straight or branched chain, saturated and unsaturated $C_{1-4}$ alkyl, alkenyl or alkynyl or aryl; each optionally substituted by hydroxy, halo, saturated or unsaturated $C_{1-4}$ alkyl, alkenyl or alkynyl, aryl, cyclo $C_{1-6}$ alkyl, carbonyl, carboxyl, amino, or amido.

In a preferred embodiment, Applicants have found that the monomer 5-ethyl-5-(hydroxymethyl)-β,β-dimethyl-1,3-dioxane-2-ethanol diacrylate (EHD) containing a cyclic acetal group, can be used to make a biomaterial (FIG. 2). The EHD biomaterial is an EHD monomer network comprised of monomers of EHD reacted with an initiator, such as benzoyl peroxide (BP) to form a cross-linked polymer network suitable for use as a biomaterial.

Another novel CAB based biomaterial discovered by Applicants is a hydrogel that is comprised of monomers of EHD and poly(ethylene glycol) diacrylate (PEGDA) copolymer (PEG-EHD Hydrogel). Hydrogels are networks of polymer chains that are able to entrap a significant volume of water. PEG-EHD hydrogels can be used as artificial matrices which are able to accomplish the major role of the extracellular matrix of natural tissues. Hydrogels perform several functions, including serving as support structures to the surrounding tissues, acting as adhesions sites for native cells, and as devices for the controlled release of biologically active molecules.

These novel cyclic acetal biomaterials are based upon a hydrolytically degradable cyclic acetal unit. It is thought that these CABs will degrade by hydrolysis of the cyclic acetal groups, forming diol and propanal degradation products that should not significantly affect the local acidity of the native tissues.

EHD was chosen because it is commercially available and contains a cyclic acetal unit. EHD is also favorable because it is a diacrylate, containing two terminal carbon-carbon double bonds. Taking advantage of the acrylate groups, EHD monomers, when reacted with the initiator benzoyl peroxide (BP) crosslink to form EHD networks, which present themselves as a rigid plastic material suitable for use as a biomaterial.

It is understood that the degradation products formed by the hydrolysis of EHD will result in a carboxylic acid, diol, and propanal. BP is a polymerization initiator commonly used with acrylates because of its ability to form free radicals. However, while the acrylates are an attractive means of polymerizing the EHD, they also cause a carboxylic acid degradation product to be formed.

The formulation of these novel EHD network biomaterials of the present invention can be accelerated by the use of conventional means, such as heat, or through the use of additives such as N,N-dimethyl-p-toluene (DMT).

It is therefore an object of the present invention to provide a novel CAB based biomaterial comprised of crosslinked CAB containing monomer subunits as shown in FIG. 1, that are suitable for use as a tissue engineering scaffold or tissue equivalent.

It is also an object of the present invention to provide a novel EHD network biomaterial comprised of crosslinked EHD monomers, that are suitable for use as a tissue engineering scaffold or tissue equivalent.

It is another object of the present invention to provide a novel biomaterial comprised of a hydrogel that is comprised of monomers of EHD and poly(ethylene glycol) diacrylate (PEGDA) that are suitable for use as a tissue engineering scaffold or tissue equivalent.

It is also an object of the present invention to provide a novel biomaterial which can degrade by hydrolysis of the cyclic acetal groups, forming diol and propanal degradation products and does not significantly affect the local acidity of the native tissues.

It is a further object of the present invention to use the novel biomaterials described herein in the orthopedic field for joint and cartilage replacement and/or repair, bone cement.

These together with other objects and advantages, which will become subsequently apparent, reside in the details of the technology as more fully hereinafter described and claimed, reference being had to the accompanying drawings forming a part hereof, wherein like numerals refer to like parts throughout.

DETAILED DESCRIPTION AND PREFERRED EMBODIMENTS

In describing embodiments of the invention, specific terminology will be resorted to for the sake of clarity. However, the invention is not intended to be limited to the specific terms so selected, and it is to be understood that each specific term includes all technical equivalents which operate in a similar manner to accomplish a similar purpose.

To overcome the major issue of acidic degradation products, a novel class of biomaterials has been created by Applicants. The novel biomaterials are based upon a hydrolytically degradable cyclic acetal unit. The biomaterials of the present invention degrade by hydrolysis of the cyclic acetal groups, forming diol and propanal degradation products that do not significantly affect the local acidity of the native tissues.

Figure 1:
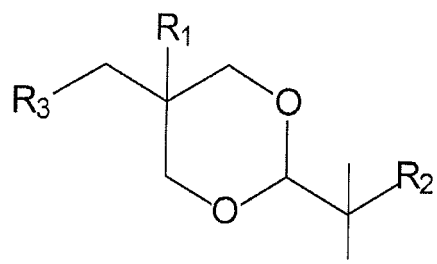
FIG. 1 is the chemical structure of the CAB monomer subunit of the present invention.

In accordance with the present invention, it has been discovered by Applicants, that novel cyclic acetyl biomaterials (CABs) can be made which are both derived from a network of monomers of compounds having hydrolytically degradable cyclic acetal units. FIG. 1 shows the CAB monomer subunit of the biomaterials of the present invention. In the figure, $R_1$ is independently selected from hydrogen or from straight chain or branched, saturated or unsaturated $C_{1-8}$ hydrocarbon optionally substituted by one or more hydroxy, halo, aryl, cyclo $C_{1-8}$ alkyl, and $R_2$ and $R_3$ both have terminal acrylate groups designated as $R_4$—OOCHC=CH$_2$, wherein $R_4$ is independently selected from hydrogen or halo; or straight or branched chain, saturated and unsaturated $C_{1-4}$ alkyl, alkenyl or alkynyl or aryl; each optionally substituted by hydroxy, halo, saturated or unsaturated $C_{1-4}$ alkyl, alkenyl or alkynyl, aryl, cyclo $C_{1-6}$ alkyl, carbonyl, carboxyl, amino, or amido.

Figure 2:
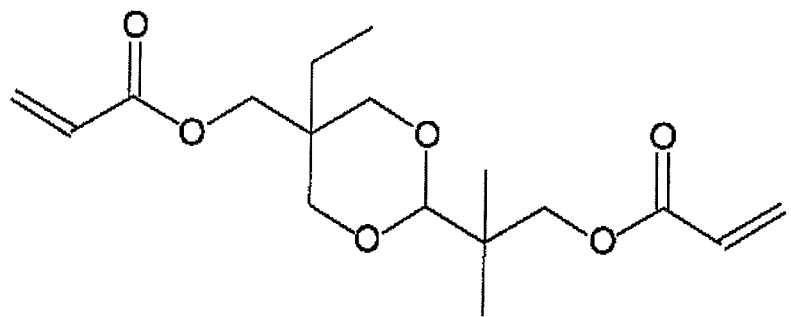
FIG. 2 is the chemical structure of the EHD polymer subunit.
Figure 4:
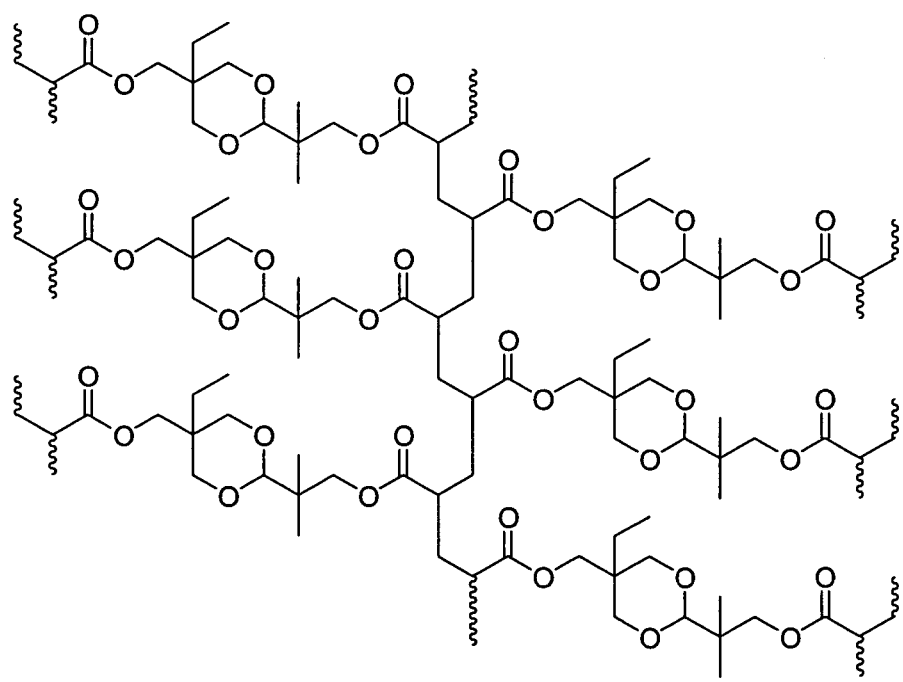
FIG. 4 is the chemical structure of a crosslinked EHD network biomaterials of the present invention.
Figure 5:
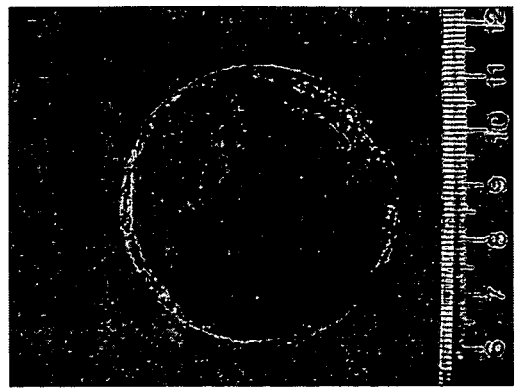
FIG. 5 is a photograph of a disc approximately 50 mm in diameter and 3 mm in thickness made from EHD network biomaterial.

EHD (FIG. 2) was chosen by Applicants due to its commercial availability and contains a cyclic acetal unit. EHD is also favorable because it is a diacrylate, containing two terminal carbon-carbon double bonds which allows the EHD monomers, when reacted with an organic peroxide initiator, such as benzoyl peroxide (BP), to crosslink and form EHD networks, which present themselves as a rigid plastic biomaterial (FIGS. 4 and 5). Other peroxide initiators can be used, such as tert-Butyl peroxide, 1,1-Bis(tert-butylperoxy)cyclohexane, and others.

Figure 6A:
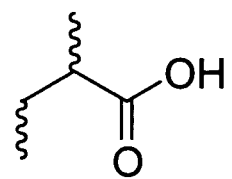
FIG. 6a is a chemical structure of a carboxylic acid degradation product of the EHD network biomaterial.
Figure 6B:
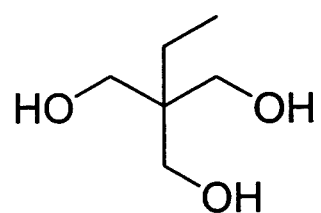
FIG. 6b is a chemical structure of a diol degradation product (2-ethyl-2-(hydroxymethyl)propane-1,3-diol) of the EHD network biomaterial.
Figure 6:
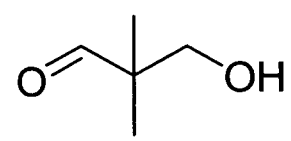
FIG. 6c is a chemical structure of an propanal degradation product (2,2-dimethyl-3-hydroxypropanal) of the EHD network biomaterial.

The degradation products formed by the hydrolysis of EHD network biomaterials are shown in FIGS. 6a-6c, and include a carboxylic acid, diol, and propanal. BP is an organic peroxide polymerization initiator commonly used with acrylates because of its ability to form free radicals. However, while the acrylates are an attractive means of polymerizing the EHD, they also cause a carboxylic acid degradation product to be formed. The formation of the EHD networks can be accelerated using heat or by the addition of N,N-dimethyl-p-toluidine (DMT) and other accelerants that work on free radicals.

General Synthesis of EHD Network Biomaterial

The following general procedure is used for preparation of the EHD network biomaterials of the present invention:
1) Dissolve BP in acetone at a concentration of between about 50 mg BP to about 300 mg/ml acetone;
2) Add the dissolved BP to a quantity of EHD in a BP/EHD ratio of about 1 wt % to about 10 wt % BP, preferably about 2 wt % to about 4 wt % BP;
3) Add additional acetone to make a concentration of about 1 g EHD to about 2 g EHD per 1 ml acetone, preferably about 1 g EHD to 1 ml acetone;
4) Mix the solution of step 3) thoroughly;
5) Pour the solution of step 4) into an appropriate mold; and
6) Gelling the solution of step 4) to make the crosslinked EHD network biomaterial.

The polymerization/crosslinking can be accelerated by the addition of DMT at a concentration range of about 1 μl to about 10 μl per g EHD, preferably at a concentration between about 2 μl to 5 μl.

It will be understood by those of ordinary skill that while acetone is a preferred solvent, any organic solvent in which both BP and EHD are generally soluble, can be used.

Applicants first studied the effects of varying the different compounds in the EHD network biomaterial formulation. Specifically, Applicants varied the initiator content, volume of diluent, and amount of accelerant according to a factorial design. The effect of these parameters on the EHD network biomaterial gelation time, maximum reaction temperature, sol fraction, degree of swelling, and cell attachment properties were measured and evaluated.

Benzoyl peroxide (BP), N,N-dimethyl-p-toluidine (DMT), 5-ethyl-5-(hydroxymethyl)-β,β-dimethyl-1,3-dioxane-2-ethanol diacrylate (EHD) were used as received from Sigma-Aldrich (Milwaukee, Wis., USA). Reagent grade acetone was used as received from Fisher Scientific (Pittsburgh, Pa., USA).

A three factor factorial design was employed. The three factors investigated were (1) weight percent of initiator, benzoyl peroxide (BP), (2) amount of diluent, acetone, and (3) amount of accelerator, N, N-dimethyl-p-toluidine (DMT). BP content was examined at two levels, 2 weight percent and 5 weight percent. The amount of diluent was studied at two levels, 0.5 mL/g EHD and 1.0 mL/g EHD. Finally, the amount of DMT was examined at three levels, 1 μL/g EHD, 4 μL/g EHD, and 8 μL/g EHD. Therefore, a 2×2×3 design with 12 formulations was used. Table 1 presents the compositions of all formulations. For the BP and diluent contents, 0 represents the low level of the factor and 1 represents the high level of the factor. For DMT, 0 represents the lowest level of the factor, 1 represents the medium level of the factor, and 2 represents the highest level of the factor.

TABLE 1

| | Initiator Content (wt %) | Diluent Content (mL/g EHD) | Accelerant Content (uL/g EHD) |
|---|---|---|---|
| | Low (0): 2 | Low (0): 0.5 | Low (0): 1 |
| | | | Medium (1): 4 |
| | High (1): 5 | High (1): 1 | High (2): 8 |
| Formulation Number | Initiator Content | Diluent Content | Accelerant Content |
| 1 | 0 | 0 | 0 |
| 2 | 0 | 0 | 1 |
| 3 | 0 | 0 | 2 |
| 4 | 0 | 1 | 0 |
| 5 | 0 | 1 | 1 |
| 6 | 0 | 1 | 2 |
| 7 | 1 | 0 | 0 |
| 8 | 1 | 0 | 1 |
| 9 | 1 | 0 | 2 |
| 10 | 1 | 1 | 0 |
| 11 | 1 | 1 | 1 |
| 12 | 1 | 1 | 2 |

EHD Network Biomaterial Synthesis

EHD network biomaterials were fabricated into disks approximately 22 mm in diameter and 4 mm thick. In order to make these disks, about 1 g of EHD was measured out. The appropriate mass of BP, depending on formulation, was dissolved in the proper amount of diluent. This solution was added to the EHD and mixed vigorously. The appropriate volume of DMT was added to the EHD solution and mixed well. The solution was then poured into a cylindrical glass vial (25 mm in diameter), where it polymerized and crosslinked (gelled).

For the cell attachment studies, a flat sheet of the EHD network biomaterials were made as previously described using 8 g of EHD. The EHD solution was poured into a mold 150 mm by 75 mm by 0.9 mm, and sandwiched between two glass plates, where it gelled. Once the networks formed in the biomaterial, circles approximately 22 mm in diameter were cut out using a cork borer. These biomaterials were washed for 10 minutes each in phosphate buffered saline (PBS), acetone, and PBS on a shaker table at 100 rpm.

Gelation Time

Figure 7:
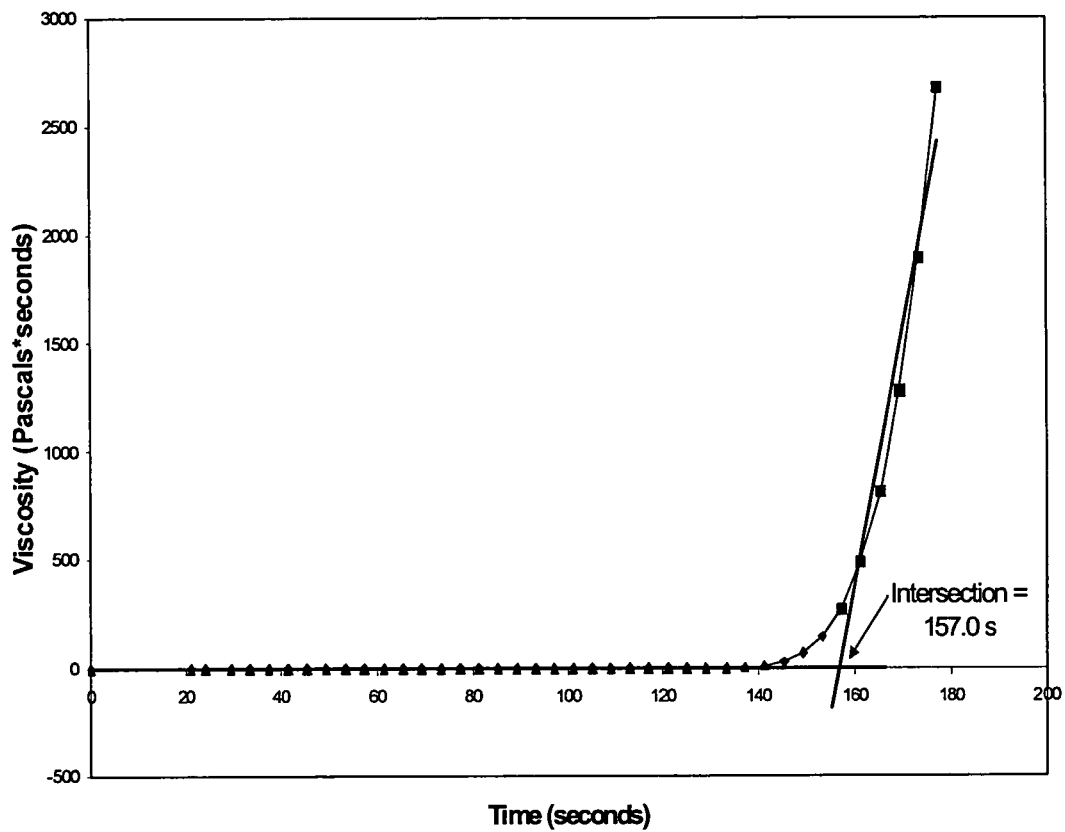
FIG. 7 is a representative gelation time plot. Gel time was defined as the x value of the intersection between a line drawn through the initial viscosity region, and a line drawn through all points where the viscosity is greater than 100 times that of the initial viscosity.

Gelation time was determined using a rheometer (Model AR 2000, TA Instruments, New Castle, Del.) equipped with a 20 mm diameter stainless steel flat plate geometry. Gelation point was defined as the time corresponding to the formation of an infinite polymer network in which all of the chains are bound together at a minimum of one site. At the gelation point, the polymer viscosity change with time asymptotically approaches infinity. A representative gelation time plot is shown in FIG. 7.

The components of each formulation in Table 1 were weighed out, using 0.5 g EHD as a basis, and the networks were formed as previously described. DMT was added at time zero and a stop watch was started at this point. The EHD solution was injected into the rheometer with the gap set to 500 µm. A time sweep was performed on each of the samples at a frequency of 20 rad/s and a constant 10% strain. Each sample type was run five times; the reported values are the mean values and the associated errors are the standard deviations.

Temperature Profiles

Figure 8:
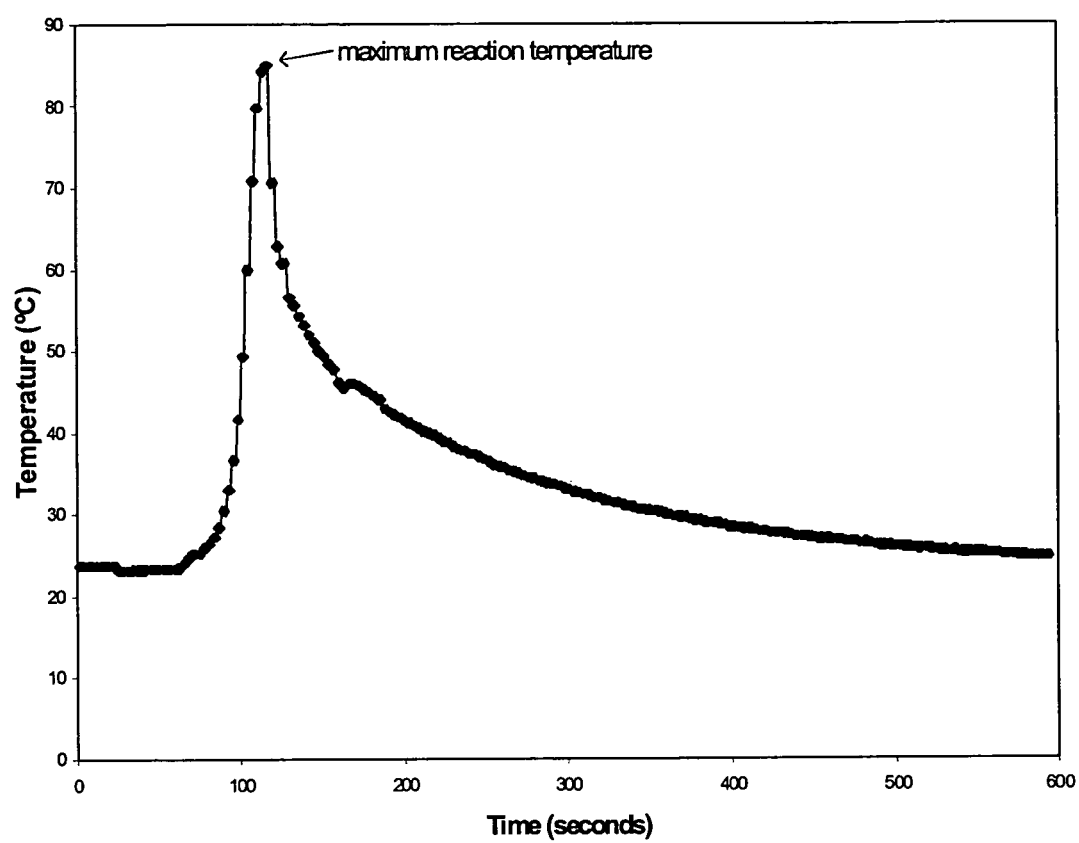
FIG. 8 is a representative temperature profile. The maximum reaction temperature for each temperature profile was determined.

The temperature of the EHD network biomaterial during the gelation time was measured using a thermocouple. The EHD biomaterial was fabricated as previously described in a 25 mm diameter glass vial. A wire thermocouple (Control Company) was inserted into the center of the sample just after the addition of DMT. The thermocouple was kept away from the bottom and sides of the glass vial. Initial temperature of the samples was 23.2±1.3° C. Temperature measurements were then taken and recorded using a Traceable Data Acquisition System (Control Company) once a second until the sample temperature returned to within 2° C. of the initial temperature. The maximum temperature was then determined for each sample. A representative temperature profile is shown in FIG. 8. Each sample type was run five times; the reported values are the mean values and the associated errors are the standard deviations.

Sol Fraction and Decree of Swelling

A study of the EHD network biomaterial sol fraction was performed using the EHD biomaterial disks, whose fabrication was described previously. Once the networks had gelled, they were patted dry with weigh paper and weighed ($W_i$). Each biomaterial sample was placed in a vial containing 10 mL of acetone, as EHD monomers are soluble in acetone. The samples were then removed from the acetone after 24 h and the surface was patted dry with weigh paper and each sample was weighed ($W_w$). The network biomaterial samples were then placed in vials and were left in a fume hood for 24 h for the remaining acetone to evaporate. Next, the samples were placed in an oven set at 60° C. and were periodically weighed until their mass stabilized ($W_d$). The sol fraction was calculated using the formula:

$$\text{Sol fraction} = \frac{W_i - W_d}{W_d} \times 100\%$$

The degree of swelling was calculated using the formula:

$$\text{Swelling degree} = \frac{W_w - W_d}{W_w} \times 100\%$$

Each biomaterial sample type was run five times; the reported values are the mean values and the associated errors are the standard deviations.

Cell Attachment

Bone marrow was harvested from the femurs and tibias of adult male Wistar Hannover GALAS rats (101-125 g). The cells were cultured in αMEM media±10% FBS in a T-75 polystyrene flask. Osteoprogenitor cells adhere to the polystyrene. Media is changed every two days, and non-adherent cells are washed away, isolating the osteoprogenitor cells. Cells were grown until confluent and passaged cells were used in the cell attachment studies.

Confluent flasks were rinsed with 2 ml of phosphate buffered saline (PBS). Cells were incubated at 37° C. for 8 minutes with 2 ml of trypsin-EDTA to release the cells from the flask. The trypsin was then neutralized with 4 ml of αMEM media+10% FBS. The cell solution was then placed in a 50 ml Falcon tube and 100 µL of the solution was removed to count the cells, using a hemacytometer. The cells were centrifuged for 5 minutes at 500 rpm. The cell pellet was resuspended in αMEM media+10% FBS.

Cells were seeded at a density of 150,000 cells/well in a 12 well plate. The experimental group was the EHD network biomaterial formulations 1, 4, 7, and 10. The biomaterial samples were prevented from floating by a 16 mm inner diameter stainless steel ring. The control was an empty polystyrene tissue culture well with the stainless steel ring.

Cell attachment was determined at 4 hours and 8 hours after initial seeding. Each well was rinsed with 0.2 mL of PBS. Cells were incubated at 37° C. for 8 minutes with 0.2 mL of trypsin to release the cells. The trypsin was the neutralized with 0.4 mL of αMEM media+10% FBS. Cells were counted using a hemacytometer. Each sample type and controls at both time points were run five times; the reported values are mean values and the associated errors are standard deviations.

Statistics

The results of the 2×2×3 factorial design were studied by an analysis of variance (ANOVA). Three factors were investigated, and therefore a total of seven effects could be identified. These include three main factor effects (the effect of BP, the effect of diluent, and the effect of DMT), three two-factor interactions (the effect of BP and diluent, the effect of BP and DMT, and the effect of diluent and DMT), and one three-factor interaction (the effect of BP, diluent, and DMT). An F value, F critical value, and p value were calculated for each of the effects. The resulting p values are reported. A significance level of 95% ($\alpha=0.05$) was chosen, therefore an effect with a p value of <0.05 is considered to be significant. While all seven effects were studied in this way, only the main effects will be discussed.

Gelation Time Results

Figure 9:
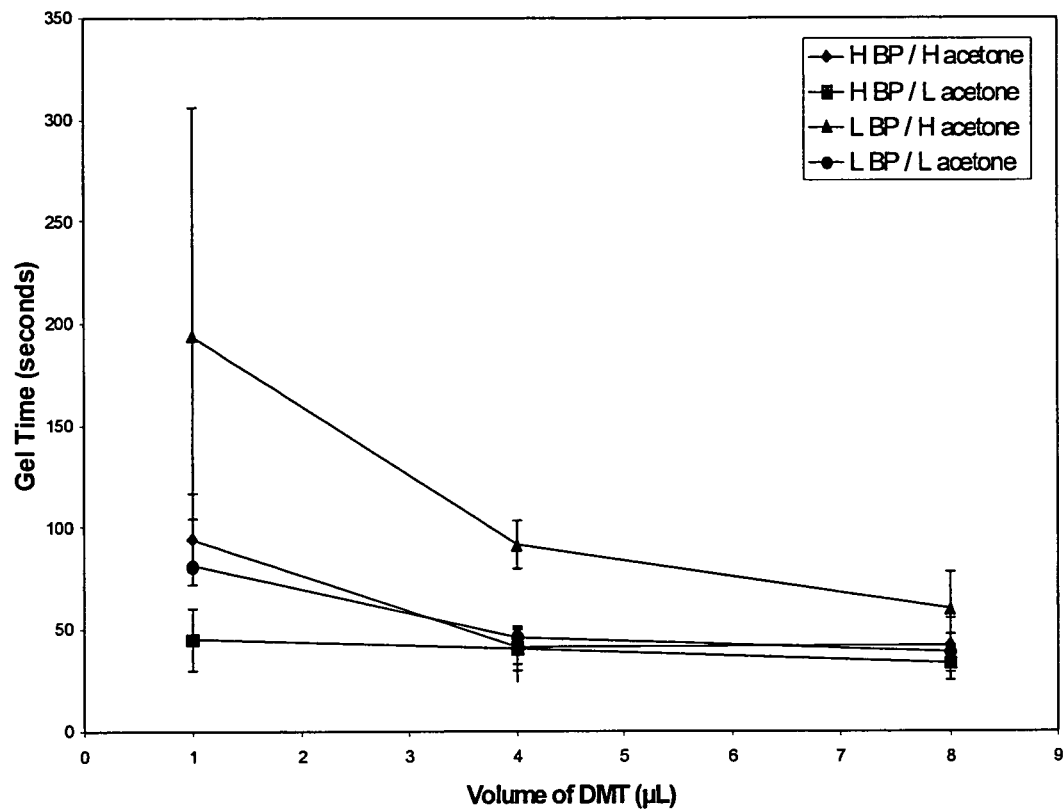
FIG. 9 shows the effect of BP content, volume of diluent, and volume of DMT on the EHD network gelation time. All factors, BP content (p=2.7×10⁻⁴), volume of diluent (p=6.9× 10⁻⁵), and volume of DMT (p=3.9×10⁻⁶) were found to be significant in determining the gelation time.

In order to measure the rate of the EHD biomaterial polymerization reaction, the gelation time for each of the EHD network biomaterial formulations was determined. The gelation time was determined by monitoring a change in the EHD solution viscosity with time. The time that the networks take to gel decreases from 194±112 s to 33±8 s as the volume of initiator, DMT, increases (FIG. 9). Analysis of the results from the factorial design study showed the main effect of BP, the main effect of diluent, and the main effect of DMT (each with p<0.05) to be statistically significant in determining the gelation time. DMT ($p=3.9\times10^{-6}$) was found to be the parameter that most affects the gelation time.

Temperature Profiles

Figure 10:
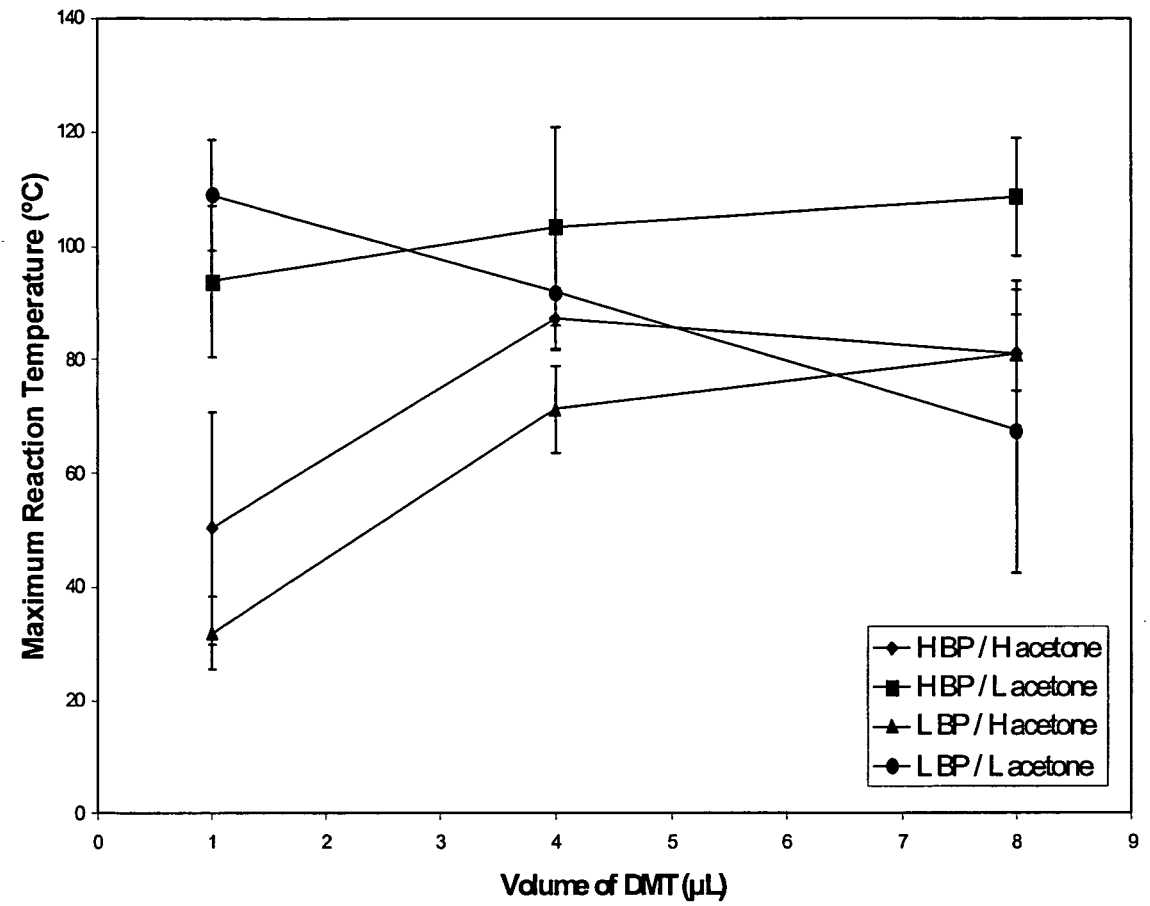
FIG. 10 shows the effect of BP content, volume of diluent, and volume of DMT on the maximum temperature reached during EHD network formation. All factors, BP content (p=1.1×10⁻³), volume of diluent (p=9.6×10⁻¹¹), and volume of DMT (p=2.4×10⁻¹⁰) were found to be significant in determining the maximum temperature.

As the EHD network biomaterials could potentially be formed in vivo, it is imperative to examine the temperature profiles of the biomaterials as they form. An important piece of information obtained from these profiles is the maximum temperature reached by the biomaterials as they formed. The maximum reaction temperature increases from 31.9±6.5° C. to 109.0±9.8° C. as the BP content increased from 2 wt % to 5 wt % and the volume of DMT increased from 1 μl/g EHD to 8 μl/g EHD (FIG. 10). Analysis of the results from the factorial design study showed the main effect of BP, the main effect of diluent, and the main effect of DMT (each with p<0.05) to be statistically significant in determining the gelation time. The volume of diluent ($p=9.6\times10^{-11}$) was found to be the parameter that most affects the maximum temperature reached by the biomaterials as they formed.

Sol Fraction Results

Figure 11:
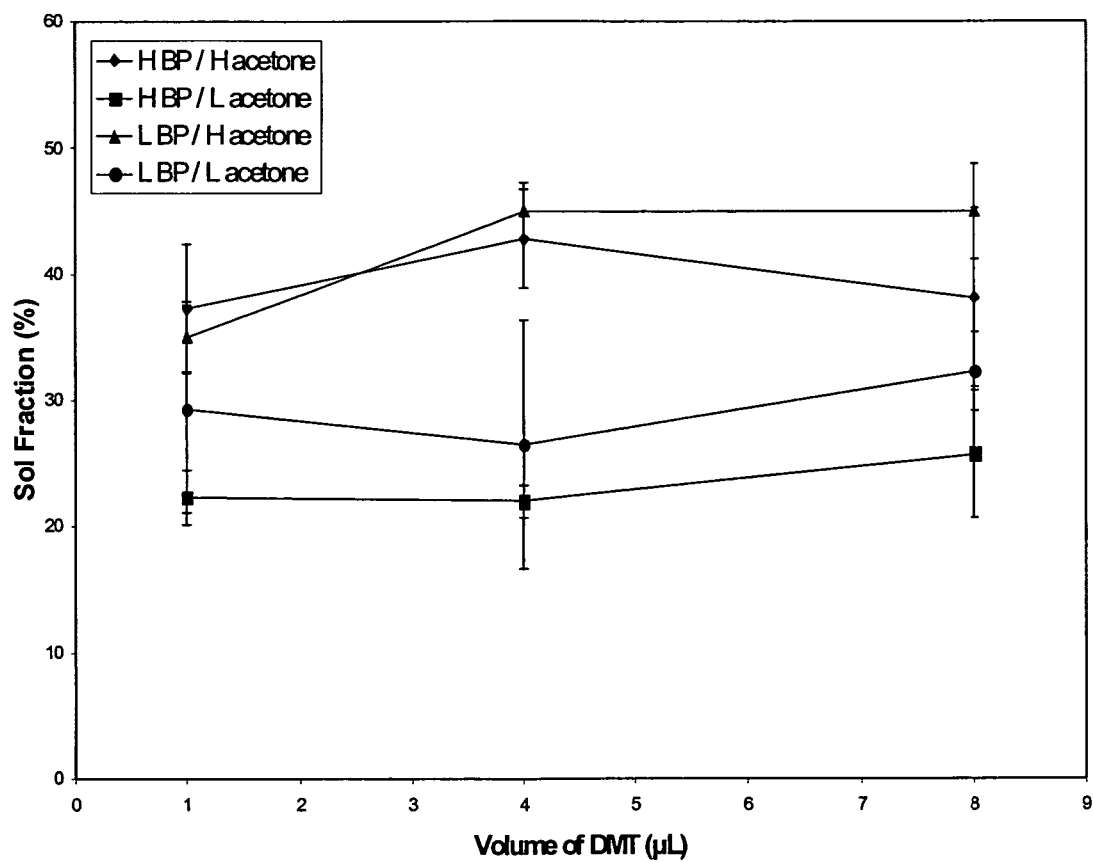
FIG. 11 shows the effects of BP content, volume of diluent, and volume of DMT on the sol fraction of the EHD networks. All factors, BP content (p=3.3×10⁻³), volume of diluent (p=4.2×10⁻¹⁴), and volume of DMT (p=3.4×10⁻²) were found to be significant in determining the sol fraction.

The sol fraction of a material is a measure of the amount of unreacted components remaining within the gelled network. A decrease in sol fraction corresponds to a decrease in the amount of unreacted material. The sol fraction of the EHD network biomaterials decreases from 45±4% to 22±2% as the BP content increased from 2 wt % to 5 wt % and the volume of diluent decreased from 1 mL/g EHD to 0.5 mL/g EHD (FIG. 11). Analysis of the results from the factorial design study showed the main effect of BP, the main effect of diluent, and the main effect of DMT (each with p<0.05) to be statistically significant in determining the sol fraction. The volume of diluent ($p=4.2\times10^{-14}$) was found to be the parameter that most affects the sol fraction.

Degree of Swelling Results

Figure 12:
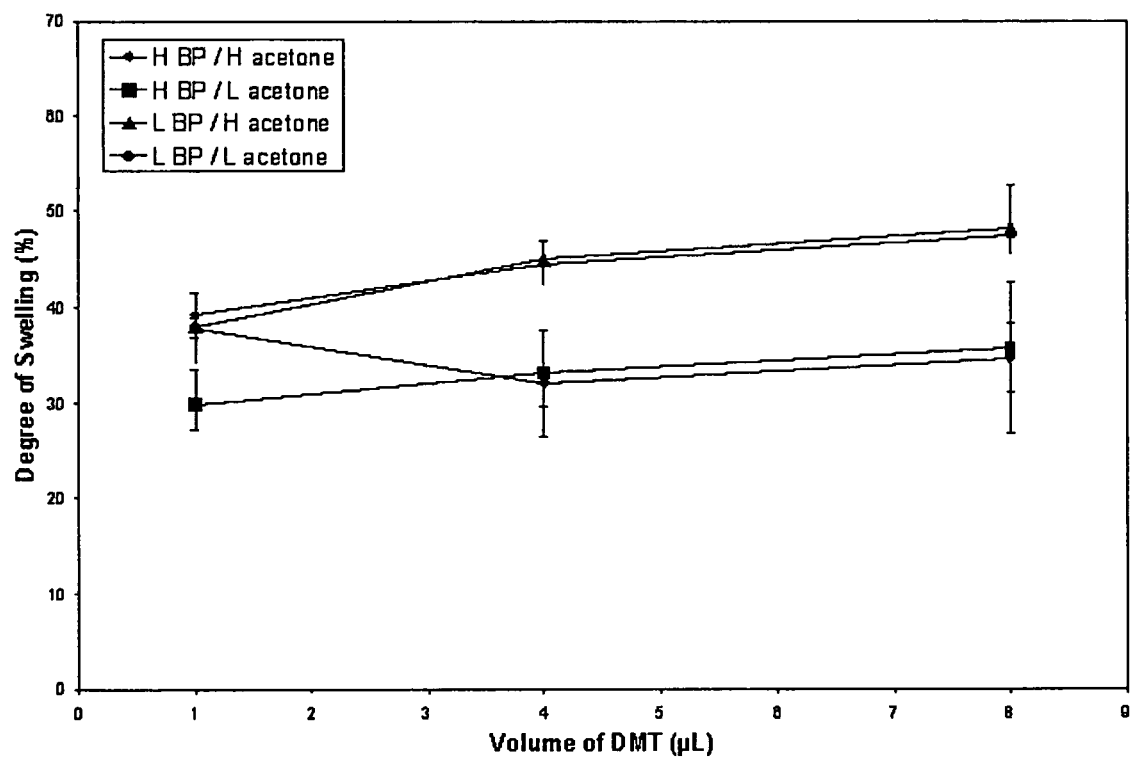
FIG. 12 shows the effects of BP content, volume of diluent, and volume of DMT on the degree of swelling of the EHD networks. The volume of diluent (p=9.3×10⁻¹³) and the volume of DMT (p=4.8×10⁻⁵) were found to be significant in determining the swelling degree. BP content (p=0.36) was not found to be significant in determining the swelling degree.

The swelling degree of a material is a measure of its ability to uptake liquid molecules and hold them between the polymer chains. The swelling degree of the EHD network biomaterial increases from 30±4% to 48±3% as the BP content decreases from 5 wt % to 2 wt %, the volume of diluent increases from 0.5 mL/g EHD to 1 mL/g EHD, and the volume of DMT increases from 1 μL/g EHD to 8 μL/g EHD (FIG. 12). Analysis of the results from the factorial design study showed the main effect of diluent and the main effect of DMT (each with p<0.05) to be statistically significant in determining the degree of swelling. The volume of diluent ($p=9.3\times10^{-13}$) was found to be the parameter that most affects the swelling degree.

Cell Attachment

Figure 13:
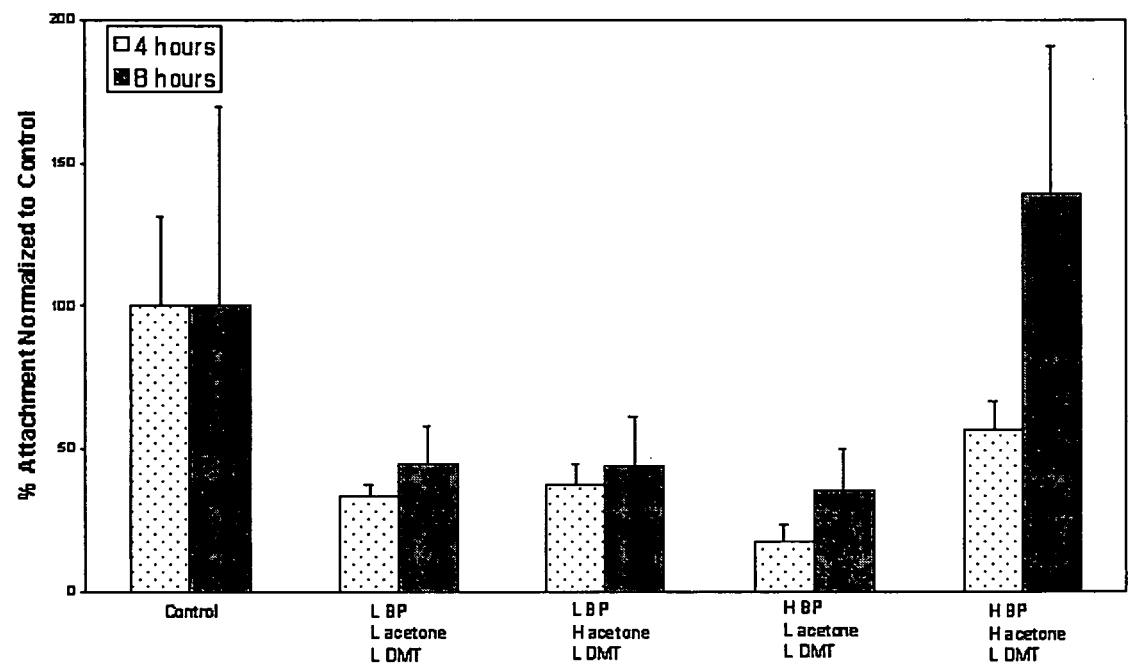
FIG. 13 is a graph detailing the cell attachment of osteoprogenitor cells on EHD networks fabricated with Formulations 1, 4, 7, and 10, determined at 4 and 8 hour time points. The results were compared with cell viability properties on a control (tissue culture polystyrene with stainless steel ring) at the same time points.

As the EHD network biomaterials can be used as prefabricated materials with osteoprogenitor cells seeded on the material before implantation, it is important to determine the cell attachment properties of the material. Cell attachment varied between 18±6% and 57±10% of the insert control at 4 hours (FIG. 13). At this time point, it was determined that there was a significant difference ($p=2.2\times10^{-10}$) in the cellular attachment between all pairs of groups except between Formulations 1 and 4.

At 8 hours, the cell attachment varied between 36±14% and 140±50% of the control (FIG. 13). At this time point, it was determined that there was a significant difference ($p=4.0\times10^{-7}$) in the cell attachment between the control and Formulations 1, 4, and 7, between the insert control and Formulations 1, 4, and 7, between Formulations 1 and 10, between Formulations 4 and 10, and between Formulations 7 and 10.

Example of Chondrocyte Cell Attachment to EHD Biomaterials

Figure 14:
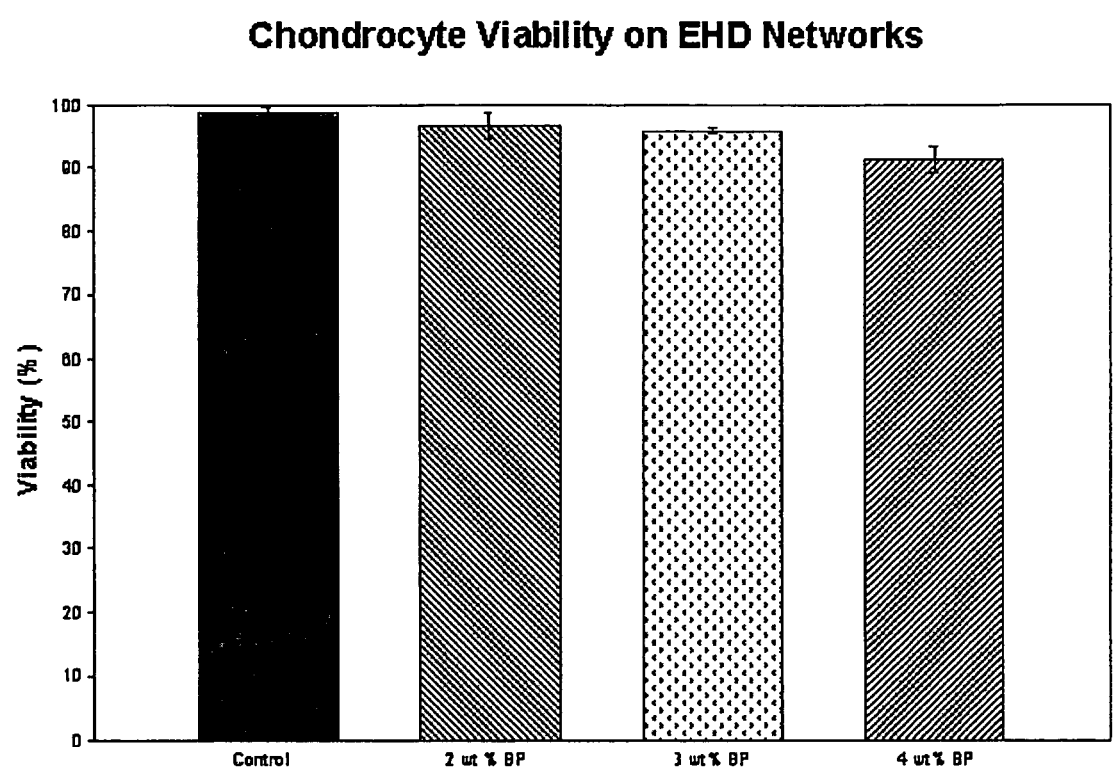
FIG. 14 is a bar graph showing the chondrocyte viability on EHD networks comparing controls to increasing concentrations of BP.

Applicants studied the ability of the EHD biomaterial to support mesenchymally derived cells. Specifically, Applicants investigated the effect of initiator content on the viability of an attached mesenchymal primary cell population. The EHD biomaterial of the present invention was rinsed with acetone and aqueous washes to prepare them for cell attachment, and sterilized with UV light exposure. Primary chondrocytes were isolated from bovine cartilage and precultured in monolayer using DMEM medium supplemented with 10% fetal bovine serum (FBS) seeded in a standard polystyrene tissue culture flask incubated at 37° C. and 5% $CO_2$. This cell population was then seeded onto the surface of the EHD network biomaterial at a concentration of about 650,000 cells per 5 cm disk. The chondrocytes were allowed to attach and proliferate on the biomaterial for two days using the same media and incubation conditions. See FIG. 14. The chondrocytes were then assayed for cell viability using a 0.4% Trypan blue stain. All samples were run in triplicate and the reported values are means and error is standard deviation.

EHD:PEGDA Copolymer Hydrogel Biomaterials (PEG-EHD)

Figure 3:
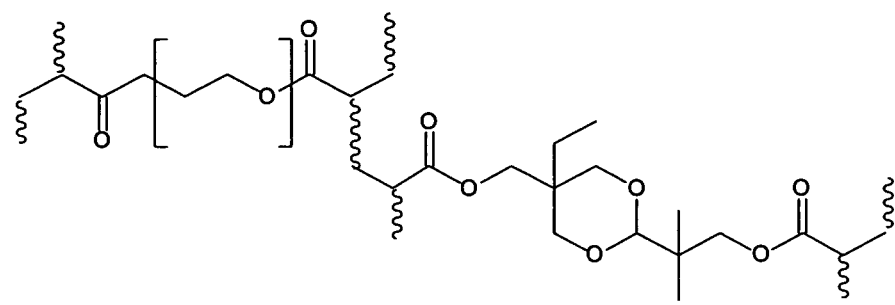
FIG. 3 is a chemical structure of the PEG-EHD hydrogel form of the biomaterial of the present invention.

The structure of PEG-EHD hydrogel biomaterial is depicted in FIG. 3. The PEG-EHD hydrogels of the present invention are made preferably, through the radical polymerization of EHD with PEGDA. The EHD monomer is used because it is a CAB and will degrade into neutral compounds. While PEGDA is used in a preferred embodiment because of hydrophilicity and biocompatibility properties, it is contemplated that other poly ester polymers can be used in making similar hydrogels. Such materials include poly(L-lactic acid), poly(glycolic acid), poly(D,L-lactic acid-glycolic acid) and poly(caprolactone).

General Synthesis of the PEG-EHD Hydrogel Biomaterial

The following general procedure is used for preparation of the PEG-EHD hydrogel biomaterials of the present invention:
1) Measure a sufficient quantity of PEGDA to effect a molar ratio of EHD:PEGDA of between about 1:1 to about 1:50;
2) Add a sufficient quantity of EHD to effect the molar ratio desired in step 1);
3) In a separate container, dissolve BP in acetone at a concentration between about 50 mg to about 300 mg BP/ml acetone;
4) Add a sufficient quantity of between about 0.1 to about 100 ml to the solution of step 2);
5) Add the dissolved BP of step 3) to the EHD/PEGDA solution of step 4) in a BP/EHD ratio of about 1 wt % to about 10 wt % BP, preferably between about 2 wt % to about 4 wt % BP;
6) Mix the solution of step 5) thoroughly;
7) Gelling the solution of step 6) to make the polymerized/crosslinked PEG-EHD hydrogel;
8) Tranfer the solution of step 7) into an appropriate mold;
9) Allowing hydrogel to form; and
10) Remove the mold.

The gelling or polymerization/crosslinking can be accelerated by the addition of DMT at a concentration range of about 1 μl to about 10 μl per g PEG-EHD, preferably at a concentration between about 2 μl to 5 μl.

Example of Engineering Skeletal Muscle Using PEG-EHD Hydrogel

Figure 15:
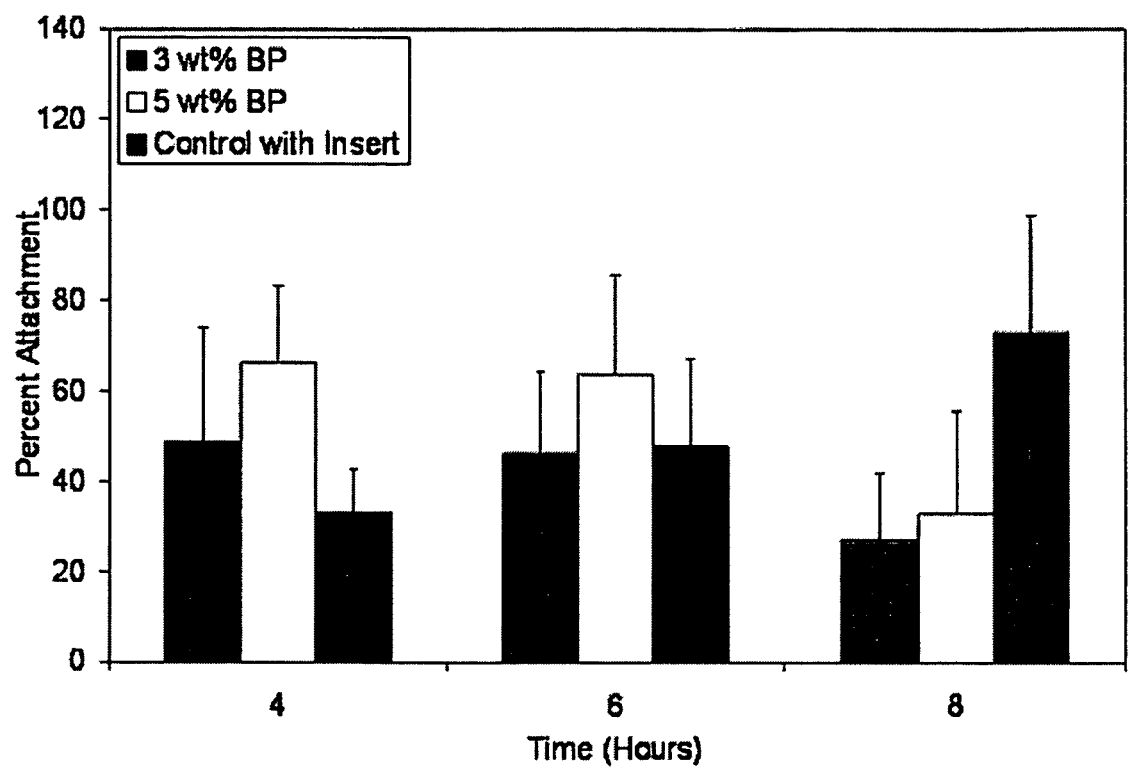
FIG. 15 is a graph showing the effect of initiator concentration on myoblastic cell attachment to EHD networks.

Applicants contemplate the use of the PEG-EHD hydrogel biomaterial composition as a scaffold for native cells to grow into new muscle tissue. In this example, Applicants conceive of a biomaterial composed of at least two different layers of biomaterials. The first or upper layer is comprised of EHD networks embedded in a PEG-EHD hydrogel. The second or lower layer is comprised of PEG-EHD hydrogels. The upper layer is engineered with the PEG-EHD hydrogel that such that cellular adhesion is facilitated. The lower layer is engineered such that cellular adhesion is inhibited. The biomaterial of the present invention was rinsed with acetone and aqueous washes to prepare them for cell attachment, and sterilized with UV light exposure. Primary myoblasts were isolated from the skeletal muscle of Wistar Hannover GALAS rats (Taconic Labs, Inc., Germantown, N.Y.) and precultured in monolayer. This cell population was then seeded at a concentration of about 100,000 cells per well in a 12 well plate. The myocytes were allowed to attach and proliferate on the biomaterial for two days in F10/HAM medium supplemented with 10% FBS and incubated at 37° C. and 5% $CO_2$. Different concentrations of BP were used to determine whether increasing initiator concentration correlates with an increase in crosslink density. The results indicate that all tested groups were similar and thus show that EHD networks can support myoblastic growth (FIG. 15).

Example of Engineering Bone Using PEG-EHD Hydrogel

Applicants contemplate the use of the PEG-EHD hydrogel biomaterial as a scaffold for native bone cells to grow repair and replace missing bone, for example, in orbital floor bone of the skull. The biomaterial of the present invention is rinsed with acetone and aqueous washes to prepare them for cell attachment, and sterilized with UV light exposure. Primary autologous osteoprogenitor cells are removed from a patient and precultured in monolayer. Once the cell population is expanded to a suitable size, the cells are then seeded onto the surface of, and in the bulk of the PEG-EHD hydrogel biomaterial. The osteoprogenitor cells attach and proliferate in and on the biomaterial. The osteoprogenitor are allowed to attach and proliferate on the biomaterial. The cells are then implanted into a patient.

The foregoing descriptions and examples should be considered as illustrative only of the principles of the invention. Since numerous applications of the present invention will readily occur to those skilled in the art, it is not desired to limit the invention to the specific examples disclosed or the exact construction and operation shown and described. Rather, all suitable modifications and equivalents may be resorted to, falling within the scope of the invention.

Having described the invention, many modifications thereto will become apparent to those skilled in the art to which it pertains without deviation from the spirit of the invention as defined by the scope of the appended claims. The disclosures of U.S. Patents, patent applications, and all other references cited above are all hereby incorporated by reference into this specification as if fully set forth in its entirety.

The invention claimed is:

1. A hydrogel tissue engineering scaffold comprising water and a crosslinked copolymer of poly(ethylene glycol) diacrylate (PEGDA) and 5-ethyl-5-(hydroxymethyl)-β,β-dimethyl-1,3-dioxane-2-ethanol diacrylate (EHD), wherein the molar ratio of EHD:PEGDA in the crosslinked copolymer is from about 1:1 to about 1:50.

2. The hydrogel tissue engineering scaffold of claim 1, further comprising proteins or nucleic acid molecules.

3. The hydrogel tissue engineering scaffold of claim 1, wherein the hydrogel tissue engineering scaffold degrades by hydrolysis of cyclic acetal groups.

4. The hydrogel tissue engineering scaffold of claim 1, wherein the hydrogel tissue engineering scaffold forms diol and propanol degradation products.

5. The hydrogel tissue engineering scaffold of claim 1, wherein the hydrogel tissue engineering scaffold does not affect local acidity of native tissues.

6. The hydrogel tissue engineering scaffold of claim 1, wherein the EHD provides rigidity to the hydrogel to provide a tissue engineering scaffold suitable for cartilage, bone, or bone cement.

7. The hydrogel tissue engineering scaffold of claim 1, wherein the EHD provides rigidity to the hydrogel to provide a tissue engineering scaffold suitable for joint and cartilage replacement and/or repair.

* * * * *